United States Patent [19]

Hurst et al.

[11] Patent Number: 4,559,348
[45] Date of Patent: Dec. 17, 1985

[54] 5- AND/OR 7-SUBSTITUTED PYRAZOLO-[4,3-b]-PYRIDINES AND THEIR USE AS ANTIINFLAMMATORY AGENTS

[75] Inventors: Jim Hurst; Josephine B. May, both of Sunderland, United Kingdom

[73] Assignee: Beecham Group, p.l.c., Brentford, England

[21] Appl. No.: 587,116

[22] Filed: Mar. 7, 1984

[30] Foreign Application Priority Data

Mar. 9, 1983 [GB] United Kingdom ............... 8306481
Oct. 29, 1983 [GB] United Kingdom ............... 8328942

[51] Int. Cl.$^4$ .................. A61K 31/415; C07D 471/04
[52] U.S. Cl. .................................... 514/303; 546/119
[58] Field of Search .................. 546/119; 424/256; 514/303

[56] References Cited

PUBLICATIONS

Foster, H. E. and Hurst, J., J. Chem. Soc. Perkin I, 2901–07, (1973), and 507–12, (1976).
Ajello, E., Journal of Heterocyclic Chemistry, vol. 8, 1035–37, (1971).
Hylton Foster and Jim Hurst, J. Chem. Soc. Perkin Trans. I, 1976(5), 507–512.

Primary Examiner—Henry R. Jiles
Assistant Examiner—Barbara Cassatt
Attorney, Agent, or Firm—James F. Haley, Jr.; Paul H. Ginsburg; Irene J. Frangos

[57] ABSTRACT

Compounds of the formula (I) and pharmaceutically acceptable salts thereof:

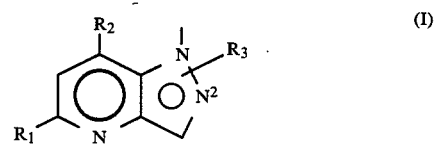

(I)

wherein:
the first of $R_1$ and $R_2$ is hydrogen, $C_{1-4}$ alkyl or phenyl optionally substituted by one or two substituents selected from halogen, $CF_3$, $C_{1-4}$ alkoxy or alkyl and the second is $SR_4$ wherein $R_4$ is phenyl optionally substituted by halogen, $CF_3$, $C_{1-4}$ alkoxy or $C_{1-4}$ alkyl, or $NR_5R_6$ wherein $R_5$ and $R_6$ are independently selected from hydrogen, $C_{1-6}$ alkyl, $C_{3-8}$ cycloalkyl, phenyl or phenyl $C_{1-4}$ alkyl either of which phenyl moieties may be substituted by one or two substituents selected from halogen, $CF_3$, $C_{1-4}$ alkoxy or $C_{1-4}$ alkyl, or $R_5$ and $R_6$ together form $C_{4-6}$ polymethylene; and
$R_3$ is hydrogen, $C_{1-4}$ alkyl or benzyl and is attached at nitrogen atom 1 or 2, having anti-inflammatory activity, a process for their preparation and their use as pharmaceuticals.

11 Claims, No Drawings

5- AND/OR 7-SUBSTITUTED PYRAZOLO-[4,3-b]-PYRIDINES AND THEIR USE AS ANTIINFLAMMATORY AGENTS

The present invention relates to pyrazolopyridines having useful pharmacological activity, to a process for their preparation and to their use as antiinflammatories.

J. Heterocycl. Chem. 1971, 8(6), 1035-7 discloses compounds of the formula (A):

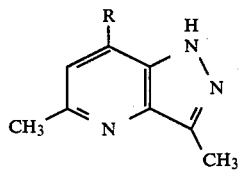

wherein R is $NH_2$, OH, $NAc_2$ or Cl. The compound wherein R is $NAc_2$ is described as having CNS antidepressant activity in mice.

A structurally distinct group of compounds have now been discovered which compounds have anti-inflammatory activity.

Accordingly, the present invention provides a compound of the formula (I) and pharmaceutically acceptable salts thereof:

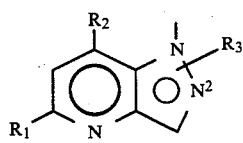

wherein:
the first of $R_1$ and $R_2$ is hydrogen, $C_{1-4}$ alkyl or phenyl optionally substituted by one or two substituents selected from halogen, $CF_3$, $C_{1-4}$ alkoxy or alkyl and the second is $SR_4$ wherein $R_4$ is phenyl optionally substituted by halogen, $CF_3$, $C_{1-4}$ alkoxy or $C_{1-4}$ alkyl, or $NR_5R_6$ wherein $R_5$ and $R_6$ are independently selected from hydrogen, $C_{1-6}$ alkyl, $C_{3-8}$ cycloalkyl, phenyl or phenyl $C_{1-4}$ alkyl either of which phenyl moieties may be substituted by one or two substituents selected from halogen, $CF_3$, $C_{1-4}$ alkoxy or $C_{1-4}$ alkyl, or $R_5$ and $R_6$ together form $C_{4-6}$ polymethylene; and
$R_3$ is hydrogen, $C_{1-4}$ alkyl or benzyl and is attached at nitrogen atom 1 or 2.

Suitable values for the first of $R_1$ and $R_2$ include hydrogen, methyl, ethyl, n- and iso-propyl and phenyl. More suitably, the first of $R_1$ and $R_2$ is hydrogen or methyl.

Suitable values for the second of $R_1$ and $R_2$ include phenylthio, 4-methylphenylthio, amino optionally substituted by one or two methyl, ethyl, n- or iso-propyl, cyclohexyl, phenyl or benzyl groups optionally substituted in the phenyl ring by one or two of chloro, bromo, $CF_3$, methoxy or methyl, or amino disubstituted by $C_4$ or $C_5$ polymethylene.

Favoured values for the second of $R_1/R_2$ include n-butylamino, anilino and 3- or 4- substituted anilino.

When $R_1$ is hydrogen or $C_{1-4}$ alkyl it is often $C_{1-4}$ alkyl, preferably methyl. When $R_2$ is hydrogen or $C_{1-4}$ alkyl it is often hydrogen.

Suitable values for $R_3$ include hydrogen, methyl, ethyl, n- and iso-propyl and benzyl. More suitably $R_3$ is hydrogen or methyl. Often $R_3$ is hydrogen.

It will be appreciated that when $R_3$ is hydrogen the compounds of formula (I) exist as tautomers, i.e. the $R_3$ hydrogen atom is labile. The compounds wherein the $R_3$ hydrogen is attached at the 1-position are normally the predominant tautomeric form, that is as formula (II):

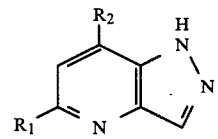

The compounds of the formula (I) can form acid addition salts with acids, such as the conventional pharmaceutically acceptable acids, for example hydrochloric, hydrobromic, phosphoric, acetic, fumaric, salicylic, citric, lactic, mandelic, tartaric and methanesulphonic.

There is a favourable group of compounds within formula (I) of formula (III):

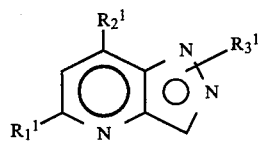

wherein $R_1^1$ is hydrogen or methyl, $R_2^1$ is $NR_5R_6$ as defined in formula (I) and $R_3^1$ is hydrogen or 2-methyl.

Suitable and preferred values for $R_2^1$ are as described for relevant $R_2$ under formula (I).

Particularly favoured values for $R_2^1$ are n-butylamino, anilino or 3- or 4- substituted anilino.

A preferred sub-group of compounds within formula (III) is of formula (IV):

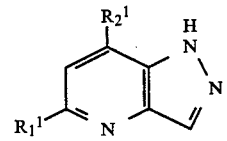

wherein $R_1^1$ and $R_2^1$ are as defined in formula (III).

A further sub-group of compounds within formula (III) is of formula (V):

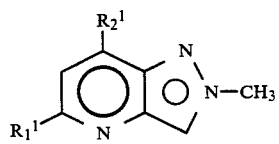

wherein $R_1^1$ and $R_2^1$ are as defined in formula (III).

A second group of compounds within formula (I) is of formula (VI):

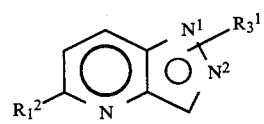

wherein $R_1^2$ is $NR_5R_5$ as defined in formula (I).

The present invention also provides a process for the preparation of a compound of formula (I) or a pharmaceutically acceptable salt thereof which process comprises the reaction of a compound of formula (VII):

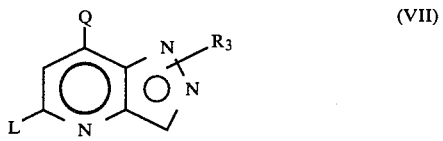

(VII)

wherein one of Q and L is a leaving group and the other is hydrogen, $C_{1-4}$ alkyl or phenyl optionally substituted by halogen, $CF_3$, $C_{1-4}$ alkoxy or $C_{1-4}$ alkyl; with $HR_7$ wherein $R_7$ is $SR_4'$ or $NR_5'R_6'$ wherein $R_4'$, $R_5'$ and $R_6'$ are $R_4$, $R_5$ and $R_6$ respectively or groups convertible thereto; and thereafter if desired or necessary converting an $R_3$ hydrogen to an $R_3$ $C_{1-4}$ alkyl group and/or converting $R_4'$ to $R_4$, $R_5'$ to $R_5$ or $R_6'$ to $R_6$ and/or forming a pharmaceutically acceptable salt thereof.

Suitable leaving groups Q/L include halogens such as chloro and bromo, preferably chloro.

The reaction may be carried out under conventional conditions for nucleophilic aromatic displacements, at elevated temperatures using excess of reagent as solvent (eg aniline) or in an inert solvent such as toluene, ethanol, pyridine, dimethylformamide, dimethylsulphoxide or dioxan.

An $R_5'$ or $R_6'$ group may be hydrogen in which case they may be converted to an $R_5$ or $R_6$ group when $C_{1-6}$ alkyl, $C_{3-8}$ cycloalkyl or phenyl $C_{1-4}$ alkyl by conventional amine alkylation or acylation followed by reduction. When and/or $R_6$ are other than hydrogen, however, it is preferred that $R_5'$ and $R_6'$ are $R_5$ and $R_6$ respectively.

When $R_5$ and $R_6$ are both hydrogen in the compound of formula (I) it is preferred that $R_5'$ is hydrogen and $R_6'$ is benzyl; the resulting compound of formula (I) wherein $R_5$ is hydrogen and $R_6$ is benzyl is then converted to the compound of formula (I) wherein $R_5$ and $R_6$ are both hydrogen by removing the $R_6$ benzyl group with hydrogen bromide.

Compounds of the formula (VII) are either known compounds or can be prepared by analogy with processes for preparing structurally similar known compounds.

For example, compounds of the formula (VII) wherein Q or L is chloro may be prepared by the phosphorus oxychloride chlorination of a compound of formula (VIII) or (IX):

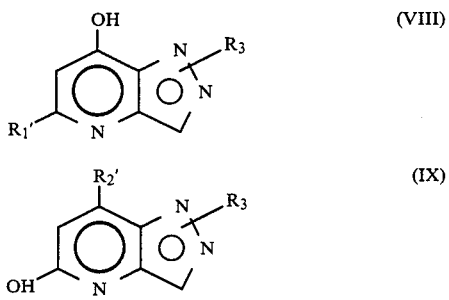

wherein $R_1'$ and $R_2'$ are hydrogen, $C_{1-4}$ alkyl or phenyl optionally substituted by one or two substituents selected from halogen, $CF_3$, $C_{1-4}$ alkoxy or $C_{1-4}$ alkyl.

Compounds of the formulae (VIII) and (IX) may be prepared as described in J. Chem. Soc. Perkin Trans. I, 1976 (5), 507 or by analogous methods thereto.

In a further aspect the invention provides a pharmaceutical composition which comprises a compound of formula (I) or a pharmaceutically acceptable salt thereof and a pharmaceutically acceptable carrier.

The compositions may be adapted for administration via the topical, oral, rectal or injection routes.

The topical anti-inflammatory compositions of this invention may contain diluents, binder, fillers, disintegrants, flavouring agents, colouring agents, lubricants, preservatives or the like in conventional manner. These conventional excipients may be employed in conventional manner, for example as in the preparation of compositions of ketoprofen, indomethacin, naproxen, acetylsalicyclic acid or other anti-inflammatory agents.

The compounds of the invention have topical anti-inflammatory activity and therefore will normally be made up into a cream, lotion, gel or ointment for topical administration to the skin comprising a compound of the formula (I) which has been formulated as a cream, lotion, gel or ointment.

Cream, lotion gel or ointment formulation that may be used for compounds of the formula (I) are conventional formulations well known in the art, for example, as described in standard text books of pharmaceutics and cosmetics, such as Harry's Cosmeticology published by Leonard Hill Books, and the British Pharmacopoeia. A standard emulsifying ointment base or anhydrous polyethylene glycol are simple examples of such suitable formulations.

These compositions may be used in the topical treatment of atopic and contact dermatitis, psoriases, acne, eczema and other inflammatory dermatoses and inflammatory conditions of eyes, ears, nose and throat.

It will be appreciated that the amount of compound of the formula (I) used will depend on a number of factors such as the nature and severity of the disorder being treated, and the specific compound being used. However, by way of illustration it is believed that effective therapy can be achieved using roughly similar amounts of the compounds of formula (I) as would be used of hydrocortisone. A typical formulation will suitably contain 0.1 to 10%, more suitably 0.5 to 5% of the compound of formula (I).

Suitably the oral compositions of this invention will be in the form of a unit dose such as a tablet, capsule or reconstitutable powder in a sachet. Such unit doses will generally contain from 10 mg to 1000 mg and more suitably will contain from about 30 mg to 500 mg for example 50 mg to 250 mg of active agent, for example about 50, 100, 150, 200, 250, 300, 350, 400, 450 or 500 mg. These compositions may be administered once or more times a day, for example 2,3 or 4 times daily, so that the total daily dose for a 70 kg adult will usually be in the range of 100 to 3000 mg and more usually in the range 30 to 300 mg, for example, 500 to 2000 mg. Alternatively the unit dose may contain from 2–20 mg of active agent and may be administered in multiples if desired to give the preceeding daily dose.

A favoured form of oral composition of this invention is a tablet containing the active agent. The active agent may be in the form of a recompressed granulate of the active ingredient in intimate mixture with a lubricant such as magnesium stearate, a filler such as microcrystalline cellulose and a disintegrant such as sodium starch glycollate.

For parenteral administration, fluid unit dosage forms are prepared utilising a compound of the formula (I) or a pharmaceutically acceptable salt thereof and a sterile vehicle. The compound, depending on the vehicle and concentration used, can be either suspended or dissolved in the vehicle, In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. Parenteral suspensions are prepared in substantially the same manner, except that the compound is suspended in the vehicle instead of being dissolved and sterilised by exposure to ethylene oxide before suspension in a sterile vehicle. Ad vantageously, a surfactant or wetting agent is included in the composition to facilitate uniform distribution of the compound.

The compositions may also contain other therapeutic agents such as anti-infective agents. Suitable anti-infective agents include the topically applicable antibacterial, anti-yeast and anti-fungal agents already in use in topical anti-inflammatory preparations.

The invention further provides a method of treatment or prophylaxis of inflammation in mammals including man which comprises the administration of a compound of formula (I) or a pharmaceutically acceptable salt thereof to the sufferer.

The invention also provides a compound of formula (I) or a pharmaceutically acceptable salt thereof for use in treating inflammation in mammals.

Mammals which may be thus treated include humans and domestic animals such as dogs, cats or horses.

Most suitably the medicament will be administered orally as 1, 3 or 4 doses per day at the dose level previously indicated.

The following Examples illustrate the invention and the following Descriptions illustrate the preparation of intermediates thereto.

Description 1

(a) 4-NITROPYRAZOLE

Pyrazole (20 g) was dissolved in concentrated sulphuric acid (150 cm$^3$). The solution was kept below 10° C. and stirred whilst a mixture of concentrated sulphuric acid (120 cm$^3$) and concentrated nitric acid (120 cm$^3$) was added dropwise. After addition of the acid the solution was gradually heated to a temperature of 120° C. and maintained at this temperature for 24 h, cooled, added to ice, basified with 20% w/v sodium carbonate, 33% w/v, ammonia and 50% w/v sodium hydroxide. The solution was extracted with ether to yield the crude product. Crystallisation from ethyl acetate (24 g, 66%) gave white plates m.p. 166°–168°.$\nu$max, 3180, 3130 (both sharp, medium intensity, N-H stretch), 1580, 1540, 1500, 1410, 1290, 995, 940, 815 and 756 cm$^{-1}$.

(b) ETHYL 3-(PYRAZOL-4-YLAMINO)CROTONATE[1]

4-Nitropyrazole (1.13 g), 10% palladium-charcoal (0.14 g), and methanol (40 cm$^3$) were shaken with hydrogen at 5 atm for 3 h. Filtration and evaporation yielded the crude 4-aminopyrazole which was treated with ethyl acetoacetate (1.43 g) and concentrated hydrochloric acid (0.2 cm$^3$). The mixture was heated on a steam bath for 5 min. to yield an oily solid. Trituration with aqueous ethanol gave the crotonate (1.31 g, 67%). Crystallisation from benzene-cyclohexane gave needles, m.p. 119°–120°. $\nu$max 3400-2500 (N-H), 1650 (C=O), 1620, 1260 (C-O), and 1160 cm$^{-1}$.

1. H. E. Foster and J. Hurst. J. Chem. Soc., Perkin I, p 511 (1976).

(c) 1,4-DIHYDRO-5-METHYLPYRAZOLO 4,3-b PYRIDIN-7-ONE[1]

Ethyl 3-(pyrazol-4-ylamino)crotonate (1.5 g) was added to boiling Dowtherm A (75 cm$^3$). The mixture was heated under reflux for 15 min. allowed to cool, and on dilution with light petroleum (b.p. 60°–80° C.) gave the pyrazolopyridone (0.78 g, 68%). The pyrazolpyridone was washed thoroughly with boiling light petroleum and crystallised from aqueous ethanol (charcoal) to give prisms, mp 330°.

M+149.0591

$\nu$max. 3500-2500 (N-H), 1605 (C=O), 1555, 1520, 1415 1265 and 945 cm$^{-1}$.

$\tau$(CF$_3$-COOH) 1.43 (1H, s, 3—H), 2.78 (1H, s, 6-H) and 7.10 (3H, s, CH$_3$).

(d) 7-CHLORO-5-METHYL-1H-PYRAZOLO 4,3-b PYRIDINE 1,4-Dihydro-5-methylpyrazolo[4,3-b]pyridin-7-one (5 g) was dried and refluxed in phosphorus oxychloride (30 ml), in dry apparatus, for 3 h. Evaporation of the solvent, followed by neutralisation with 10% w/v sodium carbonate solution gave a grey suspension. Filtration gave the chloro-compound (5 g, 89%). Sublimation (0.1 mm Hg, 120° C.) and crystallisation from ethyl acetate-ethanol (charcoal) gave white amorphous crystals m.p. 218°. $\nu$max. 3250-3000 (broad, N-H stretch), 1560 (N-H bend), 1310, 1280, 1160, 940, 880, 850, 825 and 758 cm$^{-1}$.

$\delta$ (CF$_3$ COOH) 2.99 (3H, s, 5-CH$_3$), 7.74 (1H, s, 6-H) and 8.51 (1H, s, 3-H). Total proton count 5.

Found: C, 49.89; H, 3.69; N, 25.27. C$_7$H$_6$N$_3$Cl requires C, 50.16; H, 3.62; N, 25.08; Cl 21.18%.

Description 2

7-CHLORO-1,5-DIMETHYL-1H-PYRAZOLO(4,3-b)PYRIDINE and 7-CHLORO-2,5-DIMETHYL-2H-PYRAZOLO (4,3-b)PYRIDINE A solution of methyl iodide (9.4 g) in ether (20 ml) was added to a boiling suspension of 7-chloro-5-methyl-1H-pyrazolo(4,3-b)pyridine (10 g) and sodium hydroxide (3.58 g) in 90% aqueous ethanol (20 ml) and the mixture was heated under reflux for 3 h. The solvent was removed in vacuo and the residue was extracted with boiling chloroform. The extract was dried (MgSO$_4$) and the solvent removed to give a mixture of the 1-methyl and 2-methyl compounds (11 g). The mixture (5.5 g) was separated by flash column chromatography using a column of 50 mm diameter, a 10" length of silica, and ethyl acetate as eluant; 50 ml fractions were collected. Fractions 8 to 24 gave the 1-methyl compound (3.45 g, 64%) which was sublimed (0.1 mm Hg, 120°) and then crystallised from ethyl acetate to yield white prisms, m.p. 119°–121°.

$\lambda_{max}$ (MeOH) 276 (log $\epsilon$3.74) and 304 nm (3.71).

$\nu_{max}$ 1540, 1500, 1340, 1320, 1245, 1105, 990, 890, 875, 825 cm$^{-1}$.

$\delta$ (CF$_3$COOH) 3.08 (3H, s, 5-CH$_3$), 4.68 (3H, s, 1-CH$_3$), 7.96 (1H, s, 6-H), 8.65 (1H, s, 3-H), total proton count 8.

Found: C, 52.9, H, 4.6; N, 23.1, Cl, 19.8, C$_8$H$_8$N$_3$Cl, Requires: C, 52.9; H, 4.45; N, 23.1; Cl, 19.5%.

Fractions 25-37 gave no product. The column was stripped with methanol to yield the 2-methyl compound (1.75 g, 32%) which was sublimed (0.1 mm Hg, 120°) and crystallised from ethyl acetate to yield white needles, m.p. 135°-136°.

λ$_{max}$ (MeoH), 285 (log ε4.49) and 307 nm (3.73).

ν$_{max}$ 3100, 1535, 1180, 990, 900, 860, 850, 815, 760, 655 cm$^{-1}$.

δ (CF$_3$COOH) 3.05 (3H, s, 5-CH$_3$), 4.57 (3H, s, 2-CH$_3$), 7.86 (1H, s, 6-H), 8.70 (1H, s, 3-H), total proton count 8.

Found: C, 52.8; H, 4.6; N, 22.9; Cl, 19.5. C$_8$H$_8$N$_3$Cl Requires: C, 52.9; H, 4.45; N, 23.1; Cl, 19.5%.

Description 3

(a)
4,7-Dihydro-7-oxo-1H-pyrazolo[4,3-b]pyridine-6-carboxylic acid

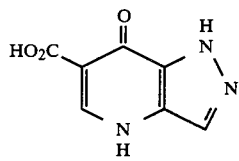

A mixture of ethyl 4,7-dihydro-7-oxo-1H-pyrazolo-[4,3-b]pyridine-6-carboxylate[1] (9.0 g, 43.5 mmol) and sodium hydroxide (3.65 g, 91 mmol) in water (60 ml) and methanol (5 ml) was heated under reflux for 90 min, then cooled, diluted with water (70 ml) and adjusted to pH 6 with 5N hydrochloric acid. The precipitated solid was collected, washed with water and dried to give the title compound as an off-white solid (7.0 g, 90%), m.p.22 330° C. (sublimes).

[1] H. E. Foster and J. Hurst, J. Chem. Soc., Perkin Trans. 1, 1976, 507.

(b) 4,7-Dihydro-7-oxo-1H-pyrazolo[4,3-b]pyridine

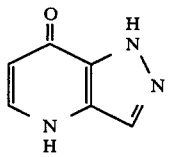

4,7-Dihydro-7-oxo-1H-pyrazolo[4,3-b]pyridine-6-carboxylic acid (7.0 g, 39 mmol) was suspended in Dowtherm A (250 ml) and the mixture was heated under reflux under nitrogen for 2.5 h. After cooling, the mixture was diluted with 60°-80° petrol and filtered. The precipitate was washed well with petrol and dried to give the crude product as an off-white solid (3.9 g, 74%). Recrystallisation from aqueous ethanol/ether gave the title compound as very fine needles, m.p.>320° C.

δ (DMSO-d$_6$): 6.0 (1H, d, J=7 Hz), 7.75 (1H, d, J=7 Hz), 7.85 (1H, s), 11.85 (1H, bs), 13.60 (1H, bs).

λ$_{max}$ (MeOH): 298 and 307 nm.

(c) 7-Chloro-1H-pyrazolo[4,3-b]pyridine

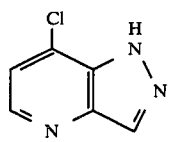

A solution of 4,7-dihydro-7-oxo-1H-pyrazolo[4,3-b]pyridine (2.0 g, 14.8 mmol) in phosphorus oxychloride (20 ml) was heated under reflux for 90 min. The excess reagent was removed in vacuo, and the residue was made slightly basic with saturated sodium hydrogen carbonate, and filtered to give a green solid. The solid was extracted with boiling ethyl acetate (2×150 ml), and the solvent was evaporated to leave the chloride as a white solid (1.55 g, 68%), m.p. >320° C.

δ (DMSO-d$_6$): 7.55 (1H, d, J=5 Hz), 8.45 (1H, s), 8.47 (1H, d, J=5 Hz).

λ$_{max}$ (MeOH): 291 nm.

EXAMPLE 1

5-Piperidino-1H-pyrazolo(4,3-b)pyridine (1)

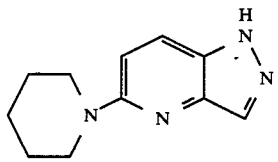

5-Chloro-1H-pyrazolo(4,3-b)pyridine (1 g) and piperidine (10 ml) were heated under reflux for 2 days. The solvent was removed in vacuo to yield a residue which was washed with water and extracted with boiling chloroform to yield the piperidino-compound (0.6 g, 46%). Crystallisation from toluene gave white crystals m.p. 217°-218°.

Found: C, 65.4; H, 7.0; N, 27.5; C$_{11}$H$_{14}$N$_4$ requires C, 65.3; H, 7.0; N, 27.7%), ν$_{max}$ 3300-3000 (broad, N-H), 1600, 1590 (strong), 1505, 1420, 1350, 1290, 1225, 1125, 960, 900, 840, 815, 780 cm$^{-1}$, δ (CD$_3$)$_2$SO 1.54 (6H, s, —CH$_2$—), 3.41 (4H, s, —CH$_2$—), 6.85 (1H, d, J9 Hz, 6-H), 7.48 (1H, d, J 9 Hz, 7-H), 7.70 (1H, s, 3-H), total proton count 13.

Found M+, 202.1218.

C$_{11}$H$_{14}$N$_{14}$ requires M, 202.1218.

EXAMPLE 2

5-Methyl-7-piperidino-1H-pyrazolo(4,3-b)pyridine (2)

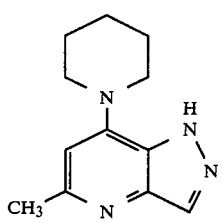

7-Chloro-5-methyl-1H-pyrazolo(4,3-b)pyridine (1 g) and piperidine (10 ml) were heated under reflux for 24 h. The piperidine was removed in vacuo to yield a pale yellow solid which was washed with water to yield the piperidino-compound (1 g, 78%), Crystallisation from ethanol-water gave pale yellow crystals, m.p. 244°. Found: C, 66.5; H, 7.55.; N, 25.7. C₁₂H₁₆N₄ requires C, 66.6; H, 7.5; N, 25.9%), $\nu_{max}$ 2660-2200 (broad), 2000-1800 (broad), 1540, 1430, 1355, 1290, 1210, 1020, 980, 810 and 760 cm⁻¹, δ (CF₃COOH) 1.97 (6H, s, —CH₂—), 2.70 (3H, s, 5 —CH₃), 4.13 (4H, s, —N—CH₂—), 6.59 (1H, s, 6-H), 8.32 (1H, s, 3-H), total proton count 15.

Found M⁺, 216.1376.

C₁₂H₁₆N₄ requires M, 216.1366.

EXAMPLE 3

5-Methyl-7-(p-tolythio)-1H-pyrazolo(4,3-b)pyridine (3)

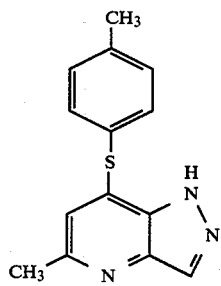

(3)

7-Chloro-5-methyl-1H-pyrazolo(4,3-b)pyridine (1 g), p-tolythiol (3.71 g) and 1,4-dioxan (20 ml) were stirred and heated under reflux for 10 h. The mixture was cooled to yield a yellow precipitate which was filtered off, suspended in water and the pH adjusted to 8 with 10% w/v sodium carbonate solution. The thio-compound (0.9 g, 59%) was filtered off and recrystallised from ethanol-ethyl acetate and then ethanol to yield a white crystalline solid, m.p. 192°-193°.

(Found: C, 65.8; H, 5.3; N, 16.3, S, 12.45. C₁₄H₁₃N₃S) requires C, 65.8, H, 5.1; N, 16.5; S, 12.6%), $\nu_{max}$ 3300-2600 (broad, N-H stretch), 1595, 1555, 1500, 1370, 1170, 1070, 950, 880, 870, 810 cm⁻¹, δ (CF₃ COOH) 2.52 (3H, s, p-CH₃), 2.76 (3H, s, 5-CH₃), 6.96 (1H, s, 6-H), 7.52 (4H, s, aromatic), 8.52 (1H, s, 3-H), total proton count 12.

Found M⁺, 255.0825

C₁₄H₁₃N₃S requires M, 255.0875.

EXAMPLE 4

7-Anilino-5-methyl-1H-pyrazolo(4,3-b)pyridine (4)

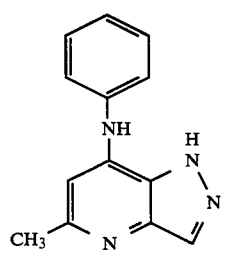

(4)

7-Chloro-5-methyl-1H-pyrazolo(4,3-b)pyridine (1 g) and aniline (20 ml) were refluxed in dry conditions under nitrogen for 18 h. Oncooling a white precipitate formed which was filtered off and washed with water to yield the anilino-compound (0.96 g, 72%). Crystallisation from ethyl acetate gave white prisms m.p. 195°-197°. (Found: C, 69.5; H, 5.5; N, 25.2. C₁₃H₁₂N₄ requires C, 69.6; H, 5.4; N, 25.0%), $\nu_{max}$ 3400 (N-H stretch), 2750-2300 (broad), 1850-1700 (broad), 1575, 1525, 1492, 1400, 925, 750, 720, 685 cm⁻¹, δ (CF₃COOH) 2.7 (3H, s, 5-CH₃), 6.84 (1H, s, 6-H), 7.53 (5H, m, aromatic), 8.42 (1H, s, 3-H), total proton count 10.

Found M⁺, 224.1063.

C₁₃H₁₂N₄ requires M, 224.1053.

EXAMPLE 5

7-Anilino-2,5-dimethyl-2H-pyrazolo(4,3-b)pyridine (5)

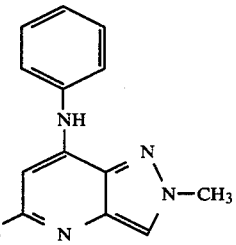

(5)

7-Chloro-2,5-dimethyl-2H-pyrazolo(4,3-b)pyridine (1 g) and aniline (20 ml) were refluxed in dry conditions under nitrogen for 3 h. The aniline was removed in vacuo to yield a yellow solid which was dissolved in water. The solution was adjusted to pH 8 with 10% w/v sodium carbonate solution and extracted with chloroform (3×75 ml). The extract was dried (MgSO₄) and the chloroform removed in vacuo to yield the anilino-compound (0.98 g, 75%). Recrystallisation from ethyl acetate-methanol gave white crystals m.p. 215°-216°.

(Found: C, 70.55; H, 5.95; N, 23.5. C₁₄H₁₄N₄ requires C, 70.55; H, 5.9; N, 23.5%), $\nu_{max}$ 3490 (N-H), 3080-3040 (broad), 1615, 1600, 1590, 1565, 1505, 1485, 1400, 1330, 1320, 1280, 1240, 1185, 1000, 870, 850, 770, 735, 700 cm⁻¹, δ (CF₃COOH) 2.68 (3H, s, 5-CH₃), 4.43 (3H, s, 2-CH₃), 6.79 (1H, s, 6-H), 7.46 (5H, s, aromatic), 8.33 (1H, s, 3-H), total proton count 13.

Found M⁺ 238.1218.

C₁₄H₁₄N₄ requires M, 238.1218.

EXAMPLE 6

7-Anilino-1,5-dimethyl-1H-pyrazolo(4,3-b)pyridine (6)

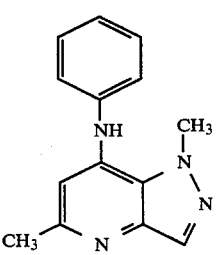

(6)

7-Chloro-1,5-dimethyl-1H-pyrazolo(4,3-b)pyridine (1 g) and aniline (20 ml) were refluxed in dry conditions under nitrogen for 3 h. The aniline was removed in vacuo to yield a yellow solid which was dissolved in water. The solution was adjusted to pH 8 with 10% w/v sodium carbonate solution and extracted with chloroform (3×75 ml). The extract was dried (MgSO₄) and the chloroform removed in vacuo to give the anilino-compound (0.95 g, 72%). Recrystallisation from ethyl acetate-light petroleum (b.p. 60°-80°) and then from ethyl acetate gave white crystals m.p. 148°-149°.

(Found: C, 70.6; H, 6.0; N, 23.5. C₁₄H₁₄N₄ requires C, 70.55; H, 5.9; N, 23.5%). ν_max. 3380 (N-H), 1600, 1570, 1500, 1435, 1365, 1290, 1240, 1000, 840, 830, 730 cm⁻¹, δ(CF₃COOH) 2.66 (3H, s, 5-CH₃), 4.68 (3H, s, 1-CH₃), 6.69 (1H, s, 6-H), 7.60 (5-H, m, aromatic), 8.35 (1H, s, 3-H), 8.41 (1H, s, N-H), total proton count 14.
Found M+, 238.1219
C₁₄H₁₄N₄ requires M, 238.1209.

EXAMPLE 7

7-(4-Ethoxyanilino)-5-methyl-1H-pyrazolo[4,3-b]pyridine (7)

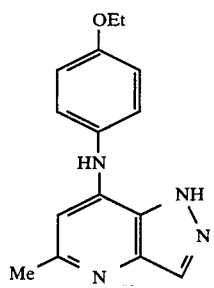

(7)

7-Chloro-5-methyl-1H-pyrazolo[4,3-b]pyridine (0.5 g, 0.003 mole) was heated at reflux temperature under nitrogen in p-phenetidine for 8 h. The mixture was left to stand at room temperature while a blue/black precipitate formed. This was collected, washed with water and ethyl acetate and the residue, a grey solid, was recrystallized from ethanol with charcoal present to give the required product as an off-white solid (0.11 g, 14%), m.p. 217° C.

δ (DMSO-d₆) 1.85 (3H, t, J=7 Hz), 2.48 (3H, s, 5-Me), 4.06 (2H, q, J=7 Hz), 6.56 (1H, s), 7.04 (2H, d, J=9 Hz), 7.36 (2H, d, J=9 Hz), 8.17 (1H, s), 10.0 (1H, broad s).
Found M+ 268.1314.
C₁₅H₁₆N₄O requires 268.1324.

EXAMPLE 8

7-(2-Methylanilino)-5-methyl-1H-pyrazolo[4,3-b]pyridine (8)

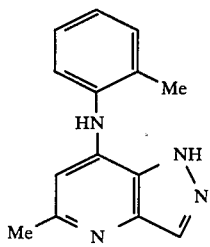

(8)

The title compound was prepared by an entirely analogous method to that employed for Example 7, using o-toluidine as the amine, with reaction time of 4 h. The product (49%) was recrystallised from ethanol/water, m.p. 300° (dec).

δ (DMSO-d₆) 2.32 (3H, s), 2.55 (3H, s), 6.21 (1H, s), 7.4 (4H, s), 8.3 (1H, s), 11.12 (1H, broad s), 14.95 (1H, broad s).
Found M+ 238.1226.
C₁₄H₁₄N₄ requires 238.1218.

EXAMPLE 9

5-Methyl-7-phenylthio-1H-pyrazolo[4,3-b]pyridine (9)

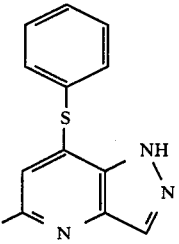

(9)

The title compound (9) was prepared by the method given in Example 3 using benzene thiol (1.64 g) and 7-chloro-5-methyl-1H-pyrazolo[4,3-b]pyridine (0.5 g). The required product (9) was obtained as a white solid (0.55 g, 76%), m.p. 196°–197° C.

δ (CF₃CO₂D) 2.73 (3H, s, 5-Me), 6.98 (1H, s, 6-H), 7.76 (5H, s, aromatic), 8.62 (1H, s, 3-H).
Found M+ 241.0679.
C₁₃H₁₁N₃S requires 241.0674.

EXAMPLE 10

7-n-Butylamino-5-methyl-1H-pyrazolo[4,3-b]pyridine (10)

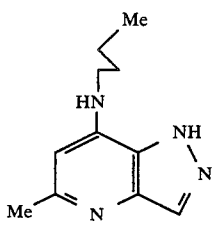

(10)

7-Chloro-5-methyl-1H-pyrazolo[4,3-b]pyridine (0.8 g, 0.0048 moles) in n-butylamine (15 ml) was heated at reflux for 39 h under nitrogen. After cooling, the excess n-butylamine was removed under reduced pressure and the resulting black oil treated with water and adjusted to pH8 (×2). The oil was extracted into boiling chloroform, treated with charcoal to give a light brown oil (0.7 g) after filtration and removal of solvent under reduced pressure. Purification by column chromatography on silica gel, initially eluting with ethyl acetate to remove high RF impurities, then rising to 20% methanol/ethyl acetate, gave a colourless oil which solidified on treatment with diethyl ether. This was further purified by recrystallisation from ethyl acetate/pentane to give the title compound as a light tan solid (0.24 g, 25%), m.p. 160°–170° C.

(Found: C,64.60; H,8.21; N,27.36. C₁₁H₁₆N₄ requires C,64.68; H,7.89; N,27.43%).

δ (CDCl₃) 0.76 (3H, t, J=7 Hz), 1.0–1.7 (4H, m), 2.55 (3H, s, 5-Me), 3.2 (2H, broad t), 6.15 (1H, s, 6-H and 1H, broad s, N-H), 7.9 (1H, s, 3-H), 9.15 (1H, broad s, N-H).
Found M+, 204.1375.
C₁₁H₁₆N₄ requires M, 204.1375.

EXAMPLE 11

7-Cyclohexylamino-5-methyl-1H-pyrazolo[4,3-b]pyridine (11)

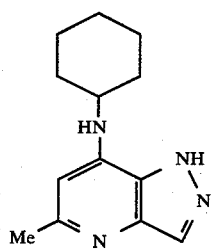
(11)

Cyclohexylamine (1.14 ml, 0.01 mole) and 7-chloro-5-methyl-1H-pyrazolo[4,3-b]pyridine (0.5 g, 0.003 mole) were heated at reflux in dry xylene (3 ml) for 48 h. The solvent was removed under reduced pressure and the residue crystallised from ethyl acetate/ether/pentane to give the title compound as a white solid (112 mg, 16%), m.p. 287°–289° C.

(Found: C,67.62; H,8.07; N,24.31. $C_{13}H_{18}N_4$ requires C,67.80; H,7.88; N,24.33%).

δ (CDCl₃/DMSO-d₆) 1.0–2.3 (10H, m), 2.52 (3H, s), 6.05 (1H, broad s), 6.18 (1H, s), 7.9 (1H, s).

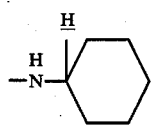

obscured by water signal 3–4.5 δ.
Found M+, 230.1539.
$C_{13}H_{18}N_4$ requires 230.1531.

EXAMPLE 12

7-(3-Ethoxyanilino)-5-methyl-1H-pyrazolo[4,3-b]pyridine (12)

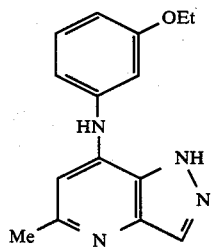
(12)

7-Chloro-5-methyl-1H-pyrazolo[4,3-b]pyridine (0.5 g, 0.003 mole) was heated at reflux in dry xylene (3 ml) under nitrogen with m-phenitidine (0.82 g, 0.77 ml) for a total of 7 h with further quantities of amine (0.3 and 0.2 ml) added after 1 h and 3 h. After cooling the resulting solid was collected and washed with ether to give the title compound as the pale yellow hydrochloride salt (0.78 g), m.p. 244°–249° C., after recrystallisation from ethanol/ethyl acetate.

A portion (0.58 g) of this salt was neutralised by dissolving in methanol/water and adding 10% sodium carbonate solution until the pH was 8. The resulting white needle crystals were collected, washed with water and dried to give the product as the hemihydrate, (0.422 g, 83%), m.p. 80°–82° C. (Found: C,64.65; H,6.11; N,20.28. $C_{15}H_{16}N_4O.\frac{1}{2}H_2O$ requires C,64.85; H,6.12; N,20.31%).

δ (DMSO-d₆) 1.36 (3H, t, J=7 Hz), 2.6 (3H, s), 4.07 (2H, q, J=7 Hz), 6.83 (1H, s), 6.8–7.6 (4H, m), 8.33 (1H, s), 11.17 (1H, broad s).
Found M+ 268.1311.
$C_{15}H_{16}N_4O$ requires 168.1324.

EXAMPLE 13

2,5-Dimethyl-7-(N-methylanilino)-2H-pyrazolo[4,3-b]pyridine (13)

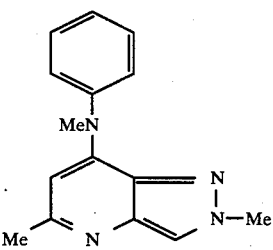
(13)

7-Chloro-2-methyl-2H-pyrazolo[4,3-b]pyridine (0.3 g, 0.00165 mole) was heated at reflux under nitrogen in freshly distilled N-methyl aniline for 18 h. As much as possible of the solvent was removed under high vacuum and the residue crystallised from ethyl acetate/ether with charcoal decolourisation to give pale yellow crystals (170 mg, 36%), m.p. 252°–256° C., of the hydrochloride salt. Neutralisation with 10% sodium carbonate solution as in Example 12, the product being extracted from the pH8 solution with chloroform (3×25 ml). The combined organic layers were washed with water, dried with anhydrous sodium sulphate, filtered and evaporated to dryness to give a pale yellow oil, which after crystallisation from ether/pentane gave the required product (77 mg, 52%), m.p. 82°–84° C.

δ (CDCl₃) 2.41 (3H, s), 3.87 (3H, s), 4.14 (3H, s), 6.09 (1H, s), 7.18–7.47 (5H, m), 7.9 (1H, s).
Found M+ 252.1364.
$C_{15}H_{16}N_4$ requires 252.1375.

EXAMPLE 14

7-(4-Chloroanilino)-5-methyl-1H-pyrazolo[4,3-b]pyridine (14)

7-Chloro-5-methyl-1H-pyrazolo[4,3-b]pyridine (1 g), 4-chloroaniline (0.76 g), and 80% aqueous-ethanol (15 ml) were heated under reflux for 12 h. The solvent was removed in vacuo to yield a yellow solid which was washed with ether. The solid was suspended in water and the pH adjusted to 9 with 20% acetic acid. 7-(4-Chloroanilino)-5-methyl-1H-pyrazolo[4,3-b]pyridine (1.48 g, 96%) was filtered off, washed with water, and recrystallised from t-butanol/petroleum ether to yield a yellow amorphous solid m.p. 240°-243°.

(Found: C,60.3; H,4.4; N,21.6; Cl,13.8. $C_{13}H_{11}N_4Cl$ requires C,60.35; H,4.3; N,21.7; Cl,13.7%), $\nu_{max}$. 2500-3400 (broad N-H), 1580, 1400, 1090, 820 cm$^{-1}$, $\delta(CF_3CO_2H)$ 2.72(3H,s,5-$CH_3$), 6.82(1H,s,6-H), 7.40(2H,d,J9 Hz, aromatic protons), 7.60(2H,d,J9 Hz, aromatic protons), 8.45(1H,s,3-H), 9.44(2H,s,NH), total proton count 11.

EXAMPLE 15

7-(4-Methoxyanilino)-5-methyl-1H-pyrazolo[4,3-b]pyridine

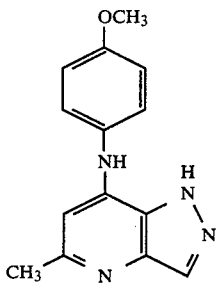

(15)

7-Chloro-5-methyl-1H-pyrazolo[4,3-b]pyridine (1.5 g), 4-methoxyaniline (1.1 g), and ethanol (20 ml) were heated under reflux for 12 h. The precipitated solid was filtered off, suspended in water, and the pH adjusted to 7.4 with acetic acid. The 7-(4-methoxyanilino)-compound (1.68 g, 74%) was filtered off, washed with water, dried, and recrystallised from ethanol/petroleum ether (charcoal) then ethanol to yield white crystals m.p. 209°-211° (Found: C,66.2; H,5.6; N,22.55. $C_{14}H_{14}N_4O$ requires C,66.1; H,5.6; N,22.0%), $_{max}$. 3300 (broad, strong N-H), 2500-3200 (N-H), 1615, 1580, 1510, 1300, 1040, 940, 850, 820 cm$^{-1}$, $\delta(CF_3CO_2H)$ 2.68(3H,s,5-$CH_3$), 4.06(3H,s,p-$OCH_3$), 6.11 (1H,s,6-H), 7.43(4H,m, aromatic protons), 8.45 (1H,s,3-H), 9.42 (2H,s,NH), total proton count 14.

EXAMPLE 16

7-(4-Methylanilino)-5-methyl-1H-pyrazolo[4,3-b]pyridine

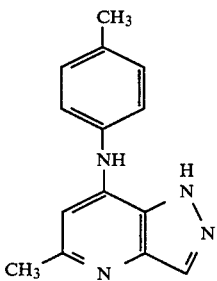

(16)

7-Chloro-5-methyl-1H-pyrazolo[4,3-b]pyridine (1.5 g), p-toluidine (0.96 g), and ethanol (20 ml) were heated under reflux for 12 h. The solvent was removed in vacuo to yield a grey solid which was suspended in water and the pH adjusted to 7.4 with acetic acid. The 7-(4-methylanilino)-compound (2.1 g, 88%) was filtered off and recrystallized from ethyl acetate/methanol to yield white crystals m.p. 220°-221°.

(Found: C,70.7; H,6.0; N,23.6. $C_{14}H_{14}N_4$ requires C,70.55; H,5.9; N,23.5%), $\nu_{max}$. 3200-3300 (broad, strong N-H), 2500-3100 (broad N-H), 1580, 1515, 1275, 945, 815 cm$^{-1}$, $\delta(CF_3CO_2H)$ 2.80(3H,s,5-$CH_3$), 3.77(3H,s,p-$CH_3$), 6.77(1H,s,6-H), 7.62(4H, m, aromatic protons), 8.25(1H,s,3-H), 9.38(2H,s,NH), total proton count 14.

EXAMPLE 17

7-(N-Methylanilino)-5-methyl-1H-pyrazolo[4,3-b]pyridine

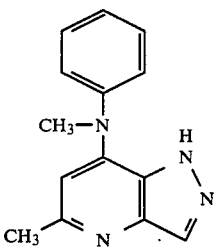

(17)

7-Chloro-5-methyl-1H-pyrazolo[4,3-b]pyridine (1 g) and N-methylaniline (15 ml) were heated under reflux for 12 h. The N-methylaniline was removed in vacuo to yield a yellow solid which was suspended in water and the pH adjusted to 9 with 20% acetic acid. The solid was filtered off, washed with water, and dried to yield the 7-(N-methylanilino)-compound (1.3 g; 91%) which on crystallisation from ethanol/petroleum ether gave a white amorphous solid m.p. 187°-188°.

(Found: C,70.4; H,6.0; N,23.4. $C_{14}H_{14}N_4$ requires C,70.55; H,5.9; N,23.5%), $\nu_{max}$. 3250 (broad N-H), 1570, 940, 710 cm$^{-1}$, $\delta(CF_3CO_2H)$ 2.80(3H,s,5-$CH_3$), 3.77(3H,s,N-$CH_3$), 6.77(1H,s,6-H), 7.62(5H,m, aromatic protons), 8.25 (1H,s,3-H), total proton count 13.

EXAMPLE 18

7-Benzylamino-5-methyl-1H-pyrazolo[4,3-b]pyridine

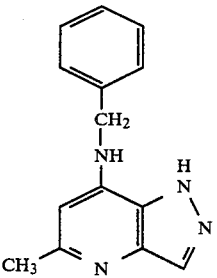

(18)

7-Chloro-5-methyl-1H-pyrazolo[4,3-b]pyridine (1 g) and benzylamine (30 ml) were heated under reflux for 6 h. The benzylamine was removed in vacuo to yield an oily solid which was digested with 20% hydrochloric acid. The digest was basified with 10% sodium carbonate solution to yield two phases. The solid in the aqueous phase was filtered off to yield the product (0.71 g). The remaining oily phase was extracted with boiling chloroform (3×20 ml) and the extract dried (MgSO$_4$) and evaporated to yield a second crop of product (0.54 g). The combined solids (1.25 g, 91%) were recrystallised from ethanol/petroleum ether to yield the 7-benzylamino-compound as white crystals m.p. 205°-206°.

(Found: C,70.7; H,6.0; N,23.3. $C_{14}H_{14}N_4$ requires C,70.55; H,5.9; N,23.5%), $\nu_{max}$. 2500-3400 (broad N-H), 1630, 1580, 1530, 945, 820, 750, 700 cm$^{-1}$, δ(CF$_3$CO$_2$H), 2.74(3H,s,5-CH$_3$), 4.86(2H,s,—CH$_2$—), 6.70(1H,s,6-H), 7.43(5H,s, aromatic protons), 8.42 (1H,s,3-H), total proton count 12.

EXAMPLE 19

7-Anilino-1H-pyrazolo[4,3-b]pyridine (19)

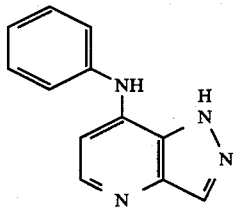

(19)

A solution of 7-chloro-1H-pyrazolo[4,3-b]pyridine (215 mg, 1.4 mmol) in aniline (1.3 ml) was heated under reflux under nitrogen for 16 h. The mixture was cooled, and the white solid which separated was collected, washed with 60°-80° petrol and water, then dried. The solid was then dissolved in 60% aqueous methanol (25 ml). The solution was filtered, adjusted to pH9 with 10% sodium carbonate solution, and on cooling the product crystallised, to give the title compound as needles (161 mg, 55%), m.p. 222°-224° C.

δ (DMSO-d$_6$): 6.90 (1H, d, J=7 Hz), 7.34 (5H, m), 8.16 (2H, s and d, J=7 Hz), 8.60 (1H, b.s).

λ$_{max}$ (MeOH): 316 nm.

EXAMPLE 20

7-Ethylamino-5-methyl-1H-pyrazolo[4,3-b]pyridine (20)

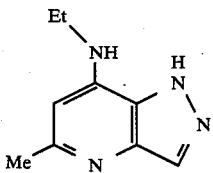

(20)

A mixture of 7-chloro-5-methyl-1H-pyrazolo[4,3-b]pyridine (1.0 g, 0.006 mole) and ethylamine 50% solution in water (100 ml) was heated under reflux for 10 days. Ethanol (50 ml) was added to the reaction mixture to facilitate solubility, and also three further quantities of ethylamine solution (3×10 ml) were added during the 10 day period. The reaction mixture was cooled and evaporated to dryness. The residue was basified to pH8-9 with 10% sodium carbonate solution and the resulting solid filtered off, dried and recrystallised from methanol/ether to give a white solid (500 mg) m.p. 244°-246° C.

δ (d$_6$-DMSO): 1.30 (3H, t, J=7 Hz), 2.51 (3H, s), 3.30 (2H, q, J=7 Hz), 6.15 (1H, s), 5.8-6.5 (2H, br.s, exchanges with D$_2$O), 7.91 (1H, s).

EXAMPLE 21

5-Methyl-7-isobutylamino-1H-pyrazolo[4,3-b]pyridine (21)

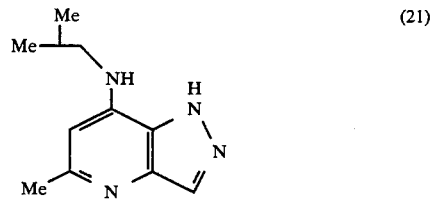

A mixture of 7-chloro-5-methyl-1H-pyrazolo[4,3-b]pyridine (1.0 g, 0.006 mole) and isobutylamine (58 g) in water (100 ml) and ethanol (50 ml) was heated under reflux for 10 days. The reaction mixture was cooled and evaporated to dryness. The oily residue was basified to pH8-9 with 10% sodium carbonate solution. The residue was extracted with ethyl acetate (3×100 ml), dried (Na$_2$SO$_4$) and evaporated to dryness to give a yellow oil. This was purified by column chromatography on alumina, and eluted with chloroform/methanol to give the desired compound as a white solid (500 mg). m.p. 162°-164° C.

δ (CDCl$_3$): 0.80 (6H, d, J=6.5 Hz), 1.45-2.11 (1H, m), 2.48 (3H, s), 2.95 (2H, d, J=6.5 Hz), 6.01 (1H, s), 5.8-6.1 (2H, br.s, exchanges with D$_2$O), 7.80 (1H, s).

EXAMPLE 22

5-Methyl-7-p-t-butylanilino-1H-pyrazolo[4,3-b]pyridine (22) was prepared in an analogous manner using p-t-butylaniline as reactant. m.p. 258°-262° C.

EXAMPLE 23

7-Amino-5-methyl-1H-pyrazolo[4,3-b]pyridine (23)

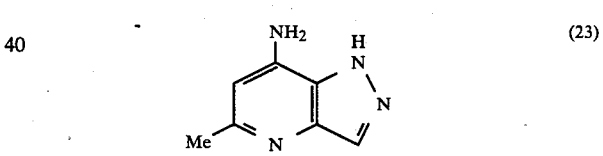

Method 1

7-Benzylamino-5-methyl-1H-pyrazolo[4,3-b]pyridine (18) (2 g) was heated at reflux for ½ h with aqueous hydrobromic acid (48%) and then as much as possible of the acid removed under reduced pressure. The remaining aqueous solution was diluted with water and neutralised with 10% sodium carbonate. After filtration and freeze drying a white solid was obtained. The required product was obtained as a white solid after column chromatography (alumina with 10% methanol/ethyl acetate as eluant).

δ (CD$_3$OD): 2.07 (3H, s), 6.07 (1H, s), 7.47 (1H, s).
λ$_{max}$ (methanol) 294 nm.
Found M+: 148.0746.
Theoretical: 148.0749.

Method 2

7-Chloro-5-methyl-1H-pyrazolo[4,3-b]pyridine (4 g, 0.024 mole) with 880 ammonia (15 ml) methanol (25 ml), and DMF (1 ml) were heated together in a sealed tube overnight at a maximum temperature of 150° C. A light brown solution had formed from the original white suspension. After cooling this solution was evaporated to dryness to give a brown oil, which solidified on standing. After crystallisation from ethyl acetate/methanol a pinkish brown solid (1.43 g) was obtained. This was identified as the hydrochloride salt of the title compound and was converted to the free base by neutralisation with 10% sodium carbonate. The resulting solid had spectroscopic characteristics identical to those obtained for the title compound in method 1.

EXAMPLE 24

7-(3,4-Dichloroanilino)-5-methyl-1H-pyrazolo[4,3-b]pyridine (24)

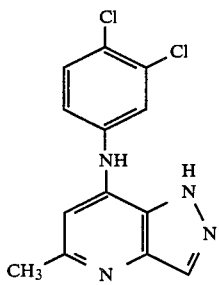

7-Chloro-5-methyl-1H-pyrazolo[4,3-b]pyridine (1.5 g) and 3,4-dichloroaniline (1.45 g) were heated under reflux in ethanol (90 ml) for 48 h. The solvent was removed in vacuo to yield a yellow solid which was suspended in water and the pH adjusted to 7.8. The solid was filtered off, washed with water, and dried to yield the 7-(3,4-dichloroanilino)-compound (2.27 g, 87%) which was recrystallised from ethanol (charcoal) to yield a white amorphous solid m.p. 273° (dec.).

(Found: C, 53.1; H, 3.5; N, 19.3; Cl, 24.1. $C_{13}H_{10}N_4Cl_2$ requires C, 53.3; H, 3.45; N, 19.1; Cl, 24.2%), $\nu_{max}$. 3400-2250 (N-H), 1630, 1580, 1530, 1410, 1400, 1310, 1135, 955, 850, 810 cm$^{-1}$, $\delta$ (CF$_3$COOH) 2.76 (3H, s, 5-CH$_3$), 6.86 (1H, s, 6-H), 7.49 (3H, m, aromatic protons), 8.46 (1H, s, 3-H), 9.47 (2H, s, N$\oplus$H$_2$), total proton count 10.

Pharmacological Data

1. Mouse Oxazolone Screen

Compounds were tested for topical anti-inflammatory activity in a mouse oxazolone screen, by a method modified from that of Dietrich and Hess [Int. Arch. Allergy, 38, 246 (1970)].

Mice were sensitised with oxazolone (2 mg in EtOH) on a shaved area of the abdomen, and then challenged with oxazolone (100 μg) with or without the test compound on the left ear 5 days later.

Weight differences between left (treated) and right (control) ears 24 hr. later gave the % inhibition shown in Table 1.

TABLE 1

| COMPOUND NO. | DOSE μg/ear | % INHIBITION |
| --- | --- | --- |
| 3 | 200 | 37*** |
| 4 | 200 | 81**** |
| 5 | 200 | 63 |
| 7 | 100 | 56* |
| 8 | 100 | 31* |
| 9 | 100 | 61* |
| 10 | 100 | 54** |
| 17 | 100 | 32 |

2. Rat Cantharidin Screen

Compounds were tested for topical anti-inflammatory activity in a cantharidin rat ear screen, by a method described by A. Boris et al, [J. Invest. Dermatol. 68, 161 (1977)].

Cantharidin (450 μg) in a suitable solvent, such as methanol or tetrahydrofuran applied topically to one rat ear, causes severe inflammation giving approximately double the normal weight at 72 hrs. compared to the other, untreated ear. The test compounds were applied simultaneously with cantharidin in tetrahydrofuran. Weight differences between treated and untreated ears 72 hrs. later gave the % inhibition shown in Table 2.

TABLE 2

| COMPOUND NO. | DOSE mg/ear | % INHIBITION |
| --- | --- | --- |
| 4 | 1 | 42*** |
| 5 | 2 | 44*** |
| 7 | 2 | 25* |
| 8 | 0.9 | 56*** |
| 9 | 1 | 40* |
| 10 | 0.5 | 76**** |
| 11 | 1 | 66* |
| 12 | 1 | 41* |
| 14 | 2 | 27* |
| 15 | 1 | 41* |
| 17 | 1 | 31* |
| 19 | 1 | 50*** |
| 22 | 1 | 68**** |
| 24 | 1 | 29* |

3. Activity in the Croton Oil Test

Compounds were tested for anti-inflammatory activity in a topical model based on that described by Fregnan G. B. and Torsello, A. L. (1975), Current Therapeutic Research 17, No. 4, 375-381. In outline the method is as follows:

Rats, Charles River Wistar Strain, female, 10/group. Weight range 200-240 g.

Irritant solution applied consists of 1% croton oil in tetrahydrofuran. 0.05 ml is placed on each ear, compound being included in the irritant solution on one ear. 6 hours later the ears are removed by cutting along the hairline and weighed.

—ve control—no irritant solution.
+ve control—irritant solution on both ears.

The results are shown in Table 3.

TABLE 3

| Compound No. | Dose mg/ear | % Inhibition |
| --- | --- | --- |
| 1 | 1 | 32.9 |
| 2 | 1 | 34.8 |
| 4 | 1 | 71.7* |

4. Activity in the Carrageenin Test

Groups of 8 OLAC Wistar male rats (140-170 g) received the Compounds orally 1 hour before 0.1 ml of 0.5% λ carrageenin injected into the right hind paw. Paw volumes were measured by mercury displacement 3 hours after carrageenin. The results are shown in Table 4.

TABLE 4

| Compound | Dose mg/kg | % Inhibition |
| --- | --- | --- |
| 1 | 88 | 34*** |
| 2 | 81 | 41.7**** |

TABLE 4-continued

| Compound | Dose mg/kg | % Inhibition |
|---|---|---|
| 4 | 75 | 40.2*** |

5. Quinone Quantal Writhing Test

L. C. Hendershot and J. Fersaith, J. Pharmac. exp. Therap. 1959, 125, 237–240.

Compounds 1 and 2 had analgesic activity giving 10 and 50 percent inhibition respectively at a dose of 50 mg/kg po.

Tests 1, 2, 3 and 4: Significantly different from the control assessed by the student's 't' test.

**** $p < 0.002$
*** $p < 0.01$
** $p < 0.02$
* $p < 0.05$

Toxicity

No toxic effects were observed in the above tests.

We claim:

1. A compound of the formula (I) and pharmaceutically acceptable salts thereof:

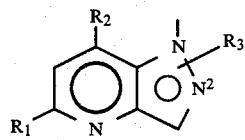

wherein:
the first of $R_1$ and $R_2$ is hydrogen, $C_{1-4}$ alkyl or phenyl optionally substituted by one or two substituents selected from halogen, $CF_3$, $C_{1-4}$ alkoxy or alkyl and the second is $SR_4$ wherein $R_4$ is phenyl optionally substituted by halogen, $CF_3$, $C_{1-4}$ alkoxy or $C_{1-4}$ alkyl, or $NR_5R_6$ wherein $R_5$ and $R_6$ are independently selected from hydrogen, $C_{1-6}$ alkyl, $C_{3-8}$ cycloalkyl, phenyl or phenyl $C_{1-4}$ alkyl either of which phenyl moieties may be substituted by one or two substituents selected from halogen, $CF_3$, $C_{1-4}$ alkoxy or $C_{1-4}$ alkyl, or $R_5$ and $R_6$ together form $C_{4-6}$ polymethylene; and
$R_3$ is hydrogen, $C_{1-4}$ alkyl or benzyl and is attached at nitrogen atom 1 or 2.

2. A compound according to claim 1 of formula (III):

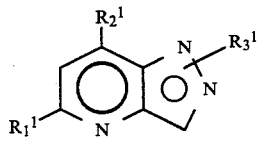

wherein $R_1^1$ is hydrogen or methyl, $R_2^1$ is $NR_5R_6$ as defined in claim 1 and $R_3^1$ is hydrogen or 2-methyl.

3. A compound according to claim 2 of formula (IV):

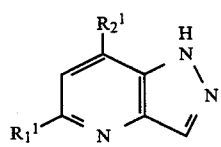

wherein $R_1^1$ and $R_2^1$ are as defined in claim 2.

4. A compound according to claim 2 of formula (V):

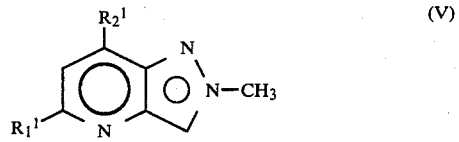

wherein $R_1^1$ and $R_2^1$ are as defined in claim 2.

5. A compound according to claim 3 wherein $R_2^1$ is anilino or 3- or 4-substituted anilino.

6. A compound according to claim 3 wherein $R_2^1$ is n-butylamino.

7. A compound selected from the group consisting of
5-Piperidino-1H-pyrazolo(4,3-b)pyridine,
5-methyl-7-piperidino-1H-pyrazolo(4,3-b)pyridine,
7-anilino-1,5-dimethyl-1H-pyrazolo(4,3-b)pyridine,
7-anilino-2,5-dimethyl-2H-pyrazolo(4,3-b)pyridine,
5-methyl-7-(p-tolythio)-1H-pyrazolo(4,3-b)pyridine,
7-(3-ethoxyanilino)-5-methyl-1H-pyrazolo[4,3-b]pyridine,
2,5-dimethyl-7-(N-methylanilino)-2H-pyrazolo[4,3-b]pyridine,
7-(4-chloroanilino)-5-methyl-1H-pyrazolo[4,3-b]pyridine,
7-(4-methoxyanilino)-5-methyl-1H-pyrazolo[4,3-b]pyridine,
7-(4-methylanilino)-5-methyl-1H-pyrazolo[4,3-b]pyridine,
7-(N-methylanilino)-5-methyl-1H-pyrazolo[4,3-b]pyridine,
7-benzylamino-5-methyl-1H-pyrazolo[4,3-b]pyridine,
5-methyl-7-isobutylamino-1H-pyrazolo[4,3-b]pyridine,
7-amino-5-methyl-1H-pyrazolo[4,3-b]pyridine and
7-(3,4-dichloroanilino)-5-methyl-1H-pyrazolo[4,3-b]pyridine,
or a pharmaceutically acceptable salt of any of the foregoing.

8. A compound selected from the group consisting of
7-anilino-5-methyl-1H-pyrazolo(4,3-b)pyridine,
7-(4-ethoxyanilino)-5-methyl-1H-pyrazolo[4,3-b]pyridine,
7-(2-methylanilino)-5-methyl-1H-pyrazolo[4,3-b]pyridine,
5-methyl-7-phenylthio-1H-pyrazolo[4,3-b]pyridine,
7-n-butylamino-5-methyl-1H-pyrazolo[4,3-b]pyridine,
7-cyclohexylamino-5-methyl-1H-pyrazolo[4,3-b]pyridine,
7-anilino-1H-pyrazolo[4,3-b]pyridine and
7-p-t-butylanilino-5-methyl-1H-pyrazolo[4,3-b]pyridine
or a pharmaceutically acceptable salt of any of the foregoing.

9. An anti-inflammatory pharmaceutical composition, comprising an anti-inflammatory effective amount of compound according to claim 1, or a pharmaceutically acceptable salt thereof, and a pharmaceutically acceptable carrier.

10. A method of treatment of inflammation in mammals which method comprises administering to the sufferer a pharmaceutically effective amount of a compound according to claim 1 or a pharmaceutically acceptable salt thereof.

11. A compound 7-ethylamino-5-methyl-1H-pyrazolo[4,3-b]pyridine or a pharmaceutically acceptable salt thereof.

* * * * *

UNITED STATES PATENT AND TRADEMARK OFFICE
CERTIFICATE OF CORRECTION

PATENT NO. : 4,559,348　　　　　　　　　Page 1 of 8
DATED : December 17, 1985
INVENTOR(S) : Hurst et al.

It is certified that error appears in the above-identified patent and that said Letters Patent is hereby corrected as shown below:

Title page, item [54], "4,3-b" should be -- [4,3-b] --;

Column 1, line 3, "4,3-b" should be -- [4,3-b] --;

Column 5, line 18, "Ad vantageously" should be -- Advantageously --;

Column 6, line 6, "4,3-b" should be -- [4,3-b] --;

Column 6, line 17, "M+" should be -- $M^+$ --;

Column 6, line 23, "4,3-b" should be -- [4,3-b] --;

Column 6, line 25, "[4,3-b]" should be -- [4,3-b] --;

Column 6, line 43, "(4,3-b)" should be -- [4,3-b] --;

Column 6, line 45, "(4,3-b)" should be -- [4,3-b] --;

Column 6, line 49, "(4,3-b)" should be -- [4,3-b] --;

Column 7, line 22, "[4,3-b]" should be -- [4,3-b] --;

Column 7, line 34, "[4,3-b]" should be -- [4,3-b] --;

Column 7, line 42, "m.p.22 330°C" should be -- m.p.>330°C --;

Column 7, line 45, "[4,3-b]" should be -- [4,3-b] --;

Column 7, line 54, "[4,3-b]" should be -- [4,3-b] --;

Column 8, line 1, "[4,3-b]" should be -- [4,3-b] --;

UNITED STATES PATENT AND TRADEMARK OFFICE
CERTIFICATE OF CORRECTION

PATENT NO. : 4,559,348
DATED : December 17, 1985
INVENTOR(S) : Hurst et al.

It is certified that error appears in the above-identified patent and that said Letters Patent is hereby corrected as shown below:

Column 8, lines 10-11, "[4,3-b]" should be -- [4,3-$\underline{b}$] --;

Column 8, line 24, "(4,3-b)" should be -- [4,3-$\underline{b}$] --

Column 8, line 34, "(4,3-b)" should be -- [4,3-$\underline{b}$] --;

Column 8, line 48, "M+" should be -- $M^+$ --;

Column 8, line 52, "(4,3-b)" should be -- [4,3-$\underline{b}$] --;

Column 8, line 64, "(4,3-b)" should be -- [4,3-$\underline{b}$] --;

Column 9, line 9, "M+" should be -- $M^+$ --;

Column 9, line 13, "(p-tolythio)" should be -- ($\underline{p}$-tolythio) --;

Column 9, line 13, "(4,3-b)" should be -- [4,3-$\underline{b}$] --;

Column 9, line 27, "(4,3-b)" should be -- [4,3-$\underline{b}$] --;

Column 9, line 28, "(p-tolythiol)" should be -- ($\underline{p}$-tolythiol) --;

Column 9, line 40, "(3H, s, p-$CH_3$)" should be -- (3H,s,$\underline{p}$-$CH_3$) --;

Column 9, line 43, "M+" should be -- $M^+$ --;

Column 9, line 47, "(4,3-b)" should be -- [4,3-$\underline{b}$] --;

Column 9, line 60, "(4,3-b)" should be -- [4,3-$\underline{b}$] --;

UNITED STATES PATENT AND TRADEMARK OFFICE
CERTIFICATE OF CORRECTION

PATENT NO. : 4,559,348
DATED : December 17, 1985
INVENTOR(S) : Hurst et al.

It is certified that error appears in the above-identified patent and that said Letters Patent is hereby corrected as shown below:

Column 9, line 62, "Oncooling" should be -- On cooling --;

Column 10, line 5, "M+" should be -- $M^+$ --;

Column 10, line 9, "(4,3-b)" should be -- [4,3-$\underline{b}$] --;

Column 10, line 22, "(4,3-b)" should be -- [4,3-$\underline{b}$] --;

Column 10, line 41, "M+" should be -- $M^+$ --;

Column 10, line 45, "(4,3-b)" should be -- [4,3-$\underline{b}$] --;

Column 10, line 58, "(4,3-b)" should be -- [4,3-$\underline{b}$] --;

Column 11, line 7, "M+" should be -- $M^+$ --;

Column 11, line 12, "[4,3-b]" should be -- [4,3-$\underline{b}$] --;

Column 11, line 27, "[4,3-b]" should be -- [4,3-$\underline{b}$] --;

Column 11, line 41, "M+" should be -- $M^+$ --;

Column 11, line 45, "[4,3-b]" should be -- [4,3-$\underline{b}$] --;

Column 11, line 67, "M+" should be -- $M^+$ --;

Column 12, line 3, "[4,3-b]" should be -- [4,3-$\underline{b}$] --;

Column 12, line 19, "[4,3-b]" should be -- [4,3-$\underline{b}$] --;

Column 12, line 25, "M+" should be -- $M^+$ --;

Column 12, line 30, "[4,3-b]" should be -- [4,3-$\underline{b}$] --;

UNITED STATES PATENT AND TRADEMARK OFFICE
CERTIFICATE OF CORRECTION

PATENT NO. : 4,559,348

DATED : December 17, 1985

INVENTOR(S) : Hurst et al.

It is certified that error appears in the above-identified patent and that said Letters Patent is hereby corrected as shown below:

Column 12, line 43, "[4,3-b]" should be -- [4,3-$\underline{b}$] --;

Column 12, line 67, "M+" should be -- $M^+$ --;

Column 13, line 3, "[4,3-b]" should be -- [4,3-$\underline{b}$] --;

Column 13, line 18, "[4,3-b]" should be -- [4,3-$\underline{b}$] --;

Column 13, line 36, "M+" should be -- $M^+$ --;

Colume 13, line 40, "[4,3-b]" should be -- [4,3-$\underline{b}$] --;

Column 13, line 54, "[4,3-b]" should be -- [4,3-$\underline{b}$] --;

Column 14, line 6, "M+" should be -- $M^+$ --;

Column 14, lines 10-11, "[4,3-b]" should be -- [4,3-$\underline{b}$] --;

Column 14, line 25, "[4,3-b]" should be -- [4,3-$\underline{b}$] --;

Column 14, line 42, "M+" should be -- $M^+$ --;

Column 14, line 46, "[4,3-b]" should be -- [4,3-$\underline{b}$] --;

Column 14, line 61, "[4,3-b]" should be -- [4,3-$\underline{b}$] --;

Column 14, line 67, "[4,3-b]" should be -- [4,3-$\underline{b}$] --;

Column 15, line 7, "(2H,d,J9Hz)" should be -- (2H,d,$\underline{J}$9Hz) -- both occurrences;

UNITED STATES PATENT AND TRADEMARK OFFICE
CERTIFICATE OF CORRECTION

PATENT NO. : 4,559,348
DATED : December 17, 1985
INVENTOR(S) : Hurst et al.

It is certified that error appears in the above-identified patent and that said Letters Patent is hereby corrected as shown below:

```
Column 15, line 13, "[4,3-b]" should be -- [4,3-b] --;

Column 15, line 27, "[4,3-b]" should be -- [4,3-b] --;

Column 15, line 39, "(3H,s,p-OCH3)" should be
-- (3H,s,p-OCH3) --;

Column 15, line 44, "[4,3-b]" should be -- [4,3-b] --;

Column 15, line 59, "[4,3-b]" should be -- [4,3-b] --;

Column 15, line 60, "p-toluidine" should be
-- p-toluidine --;

Column 16, line 3, "(3H,s,p-CH3)" should be
-- (3H,s,p-CH3) --;

Column 16, line 8, "[4,3-b]" should be -- [4,3-b] --;

Column 16, line 23, "[4,3-b]" should be -- [4,3-b] --;

Column 16, line 39, "[4,3-b]" should be -- [4,3-b] --;

Column 16, line 54, "[4,3-b]" should be -- [4,3-b] --;

Column 17, line 8, "[4,3-b]" should be -- [4,3-b] --;

Column 17, line 21, "[4,3-b]" should be -- [4,3-b] --;

Column 17, line 39, "[4,3-b]" should be -- [4,3-b] --;

Column 17, lines 51-52, "[4,3-b]" should be -- [4,3-b] --;
```

UNITED STATES PATENT AND TRADEMARK OFFICE
CERTIFICATE OF CORRECTION

PATENT NO. : 4,559,348

DATED : December 17, 1985    Page 6 of 8

INVENTOR(S) : Hurst et al.

It is certified that error appears in the above-identified patent and that said Letters Patent is hereby corrected as shown below:

Column 18, line 3, "[4,3-b]" should be -- [4,3-$\underline{b}$] --;

Column 18, lines 15-16, "[4,3-b]" should be -- [4,3-$\underline{b}$] --;

Column 18, line 32, "-p-t" should be -- -$\underline{p}$-t --;

Column 18, line 32, "[4,3-b]" should be -- [4,3-$\underline{b}$] --;

Column 18, line 34, "-p-t" should be -- -$\underline{p}$-t --;

Column 18, line 37, "[4,3-b]" should be -- [4,3-$\underline{b}$] --;

Column 18, line 48, "[4,3-b]" should be -- [4,3-$\underline{b}$] --;

Column 18, line 60, "M+" should be -- $M^{+}$ --;

Column 18, line 64, "[4,3-b]" should be -- [4,3-$\underline{b}$] --;

Column 19, line 13, "[4,3-b]" should be -- [4,3-$\underline{b}$] --;

Column 19, line 28, "[4,3-b]" should be -- [4,3-$\underline{b}$] --;

Column 22, line 16, "(4,3-b)" should be -- [4,3-$\underline{b}$] --;

Column 22, line 17, "(4,3-b)" should be -- [4,3-$\underline{b}$] --;

Column 22, line 18, "(4,3-b)" should be -- [4,3-$\underline{b}$] --;

Column 22, line 19, "(4,3-b)" should be -- [4,3-$\underline{b}$] --;

Column 22, line 20, "p-tolythio" should be -- $\underline{p}$-tolythio --;

UNITED STATES PATENT AND TRADEMARK OFFICE
CERTIFICATE OF CORRECTION

PATENT NO. : 4,559,348

DATED : December 17, 1985

INVENTOR(S) : Hurst et al.

Page 7 of 8

It is certified that error appears in the above-identified patent and that said Letters Patent is hereby corrected as shown below:

Column 22, line 20, "(4,3-b)" should be -- [4,3-$\underline{b}$] --;

Column 22, lines 21-22, "[4,3-b]" should be -- [4,3-$\underline{b}$] --;

Column 22, lines 23-24, "[4,3-b]" should be -- [4,3-$\underline{b}$] --;

Column 22, line 25, "[4,3-b]" should be -- [4,3-$\underline{b}$] --;

Column 22, lines 27-28, "[4,3-b]" should be -- [4,3-$\underline{b}$] --;

Column 22, lines 29-30, "[4,3-b]" should be -- [4,3-$\underline{b}$] --;

Column 22, lines 31-32, "[4,3-b]" should be -- [4,3-$\underline{b}$] --;

Column 22, line 33, "[4,3-b]" should be -- [4,3-$\underline{b}$] --;

Column 22, line 34, "[4,3-b]" should be -- [4,3-$\underline{b}$] --;

Column 22, line 36, "[4,3-b]" should be -- [4,3-$\underline{b}$] --;

Column 22, lines 37-38, "[4,3-b]" should be -- [4,3-$\underline{b}$] --;

Column 22, line 41, "(4,3-b)" should be -- [4,3-$\underline{b}$] --;

Column 22, lines 42-43, "[4,3-b]" should be -- [4,3-$\underline{b}$] --;

Column 22, lines 44-45, "[4,3-b]" should be -- [4,3-$\underline{b}$] --;

Column 22, line 46, "[4,3-b]" should be -- [4,3-$\underline{b}$] --;

Column 22, line 47, "n" should be -- $\underline{n}$ --;

UNITED STATES PATENT AND TRADEMARK OFFICE
CERTIFICATE OF CORRECTION

PATENT NO. : 4,559,348

DATED : December 17, 1985

INVENTOR(S) : Hurst et al.

It is certified that error appears in the above-identified patent and that said Letters Patent is hereby corrected as shown below:

Column 22, line 47, "[4,3-b]" should be -- [4,3-$\underline{b}$] --;

Column 22, lines 49-50, "[4,3-b]" should be -- [4,3-$\underline{b}$] --;

Column 22, line 51, "[4,3-b]" should be -- [4,3-$\underline{b}$] --;

Column 22, line 52, "p-t" should be -- $\underline{p}$-t --;

Column 22, line 52, "[4,3-b]" should be -- [4,3-$\underline{b}$] --;

Column 22, line 66, "[4,3-b]" should be -- [4,3-$\underline{b}$] --;

Signed and Sealed this

Twenty-first Day of February, 1989

Attest:

DONALD J. QUIGG

*Attesting Officer*     *Commissioner of Patents and Trademarks*